United States Patent [19]
Berns

[11] Patent Number: 5,851,185
[45] Date of Patent: Dec. 22, 1998

[54] APPARATUS FOR ALIGNMENT OF TUBULAR ORGANS

[75] Inventor: Mark I. Berns, Northbrook, Ill.

[73] Assignee: Cabot Technology Corporation, Wilmington, Del.

[21] Appl. No.: 886,438

[22] Filed: Jul. 2, 1997

[51] Int. Cl.$^6$ ....................................................... A61B 5/00
[52] U.S. Cl. ........................................................... 600/434
[58] Field of Search .................................. 600/433, 434, 600/585; 604/264, 95

[56] References Cited

U.S. PATENT DOCUMENTS

| | | | |
|---|---|---|---|
| 4,790,809 | 12/1988 | Kuntz | 604/8 |
| 5,185,005 | 2/1993 | Ballantyne | 604/174 |
| 5,269,759 | 12/1993 | Hernandez et al. | 604/96 |
| 5,492,538 | 2/1996 | Johlin, Jr. | 604/264 |
| 5,507,731 | 4/1996 | Hernandez et al. | 604/264 |
| 5,606,980 | 3/1997 | Calhoun et al. | 128/772 |
| 5,607,406 | 3/1997 | Hernandez et al. | 604/264 |
| 5,624,430 | 4/1997 | Eton et al. | 600/585 |

OTHER PUBLICATIONS

Thomas A. Londergan et al., "Early Fluoroscopic Realignment for Traumatic Urethral Injuries", *Urology*, 49:101–103, 1997.

*Primary Examiner*—Max Hindenburg
*Assistant Examiner*—Charles Marmor, II
*Attorney, Agent, or Firm*—Austin R. Miller

[57] ABSTRACT

An apparatus is provided for aligning a damaged tubular organ. One component includes a magnetically attractable element and another component includes means for generating a magnetic field sufficient to attract the magnetically attractable element. In use, one component is inserted toward a damaged region of a tubular organ and the other component is inserted through another segment of the tubular organ toward the damaged region. The components attract one another to engage one another along a substantially common axis in order to align the tubular organ along that axis.

22 Claims, 12 Drawing Sheets

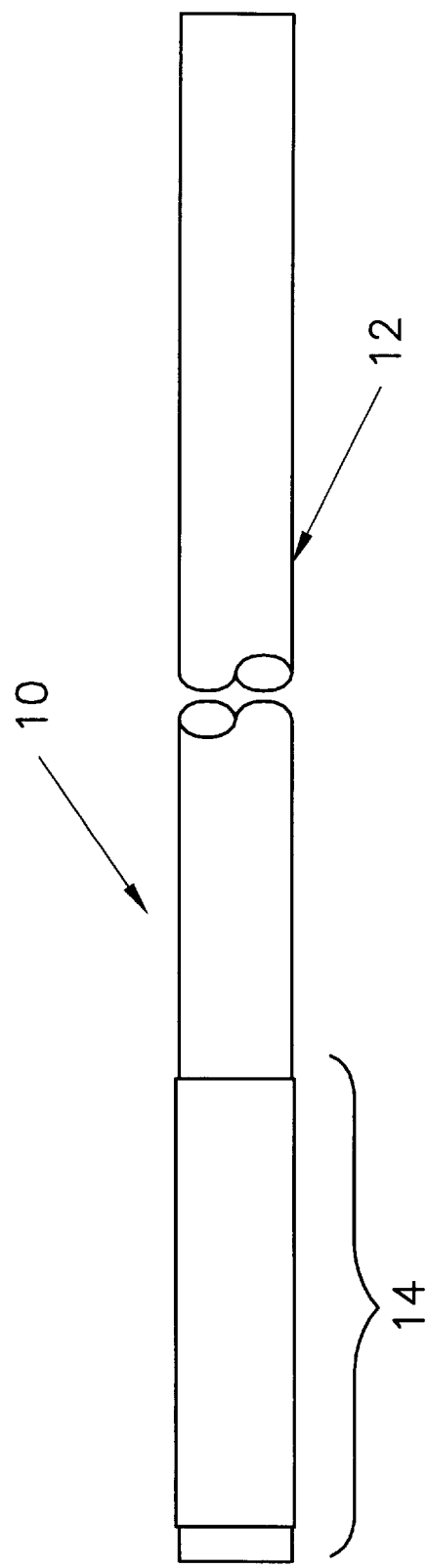
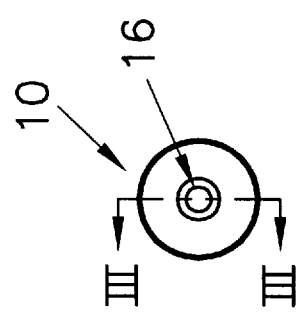

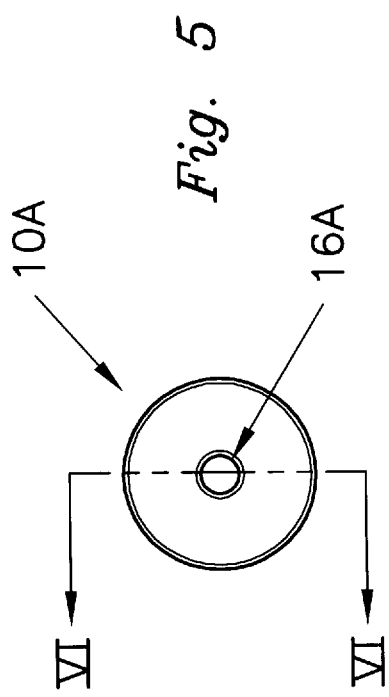
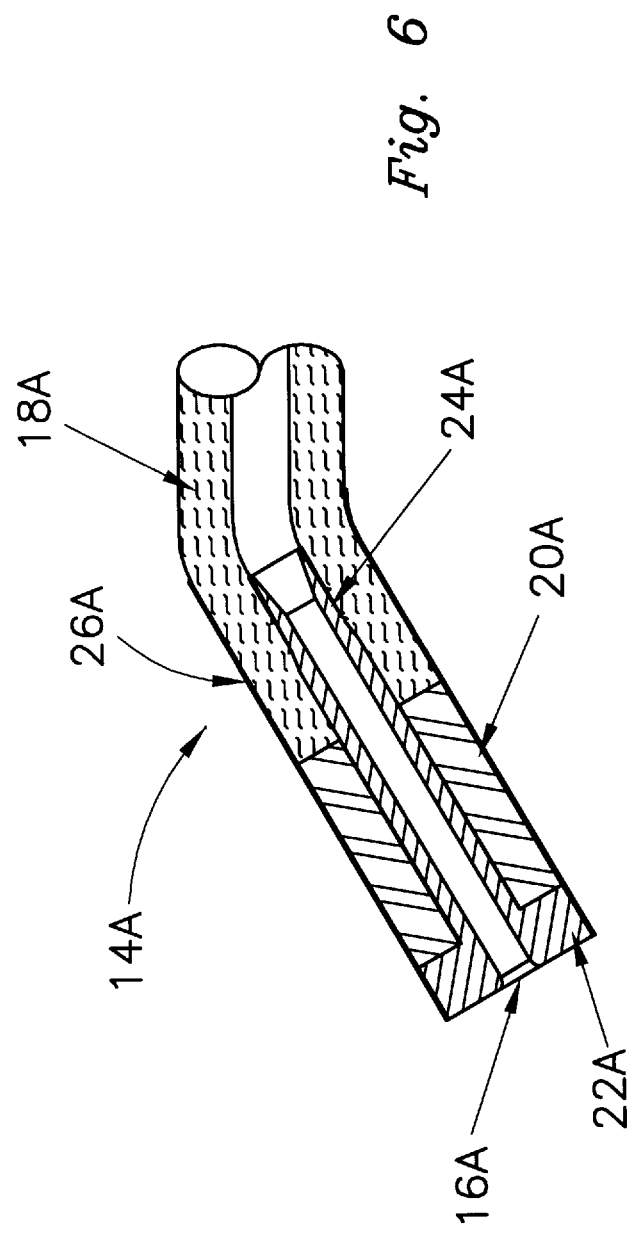

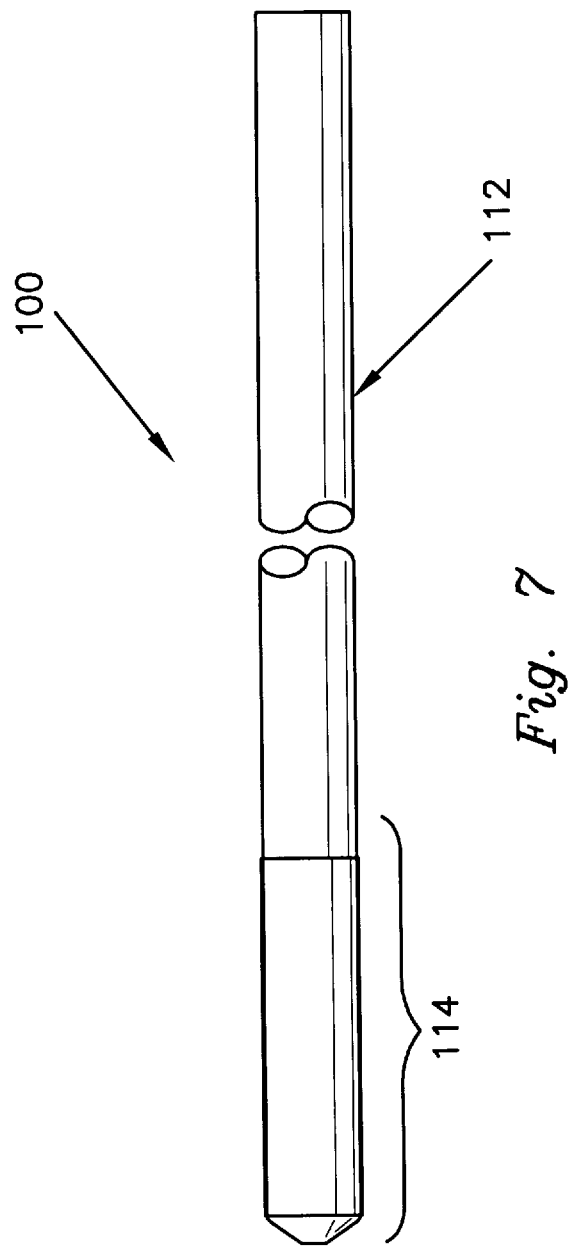

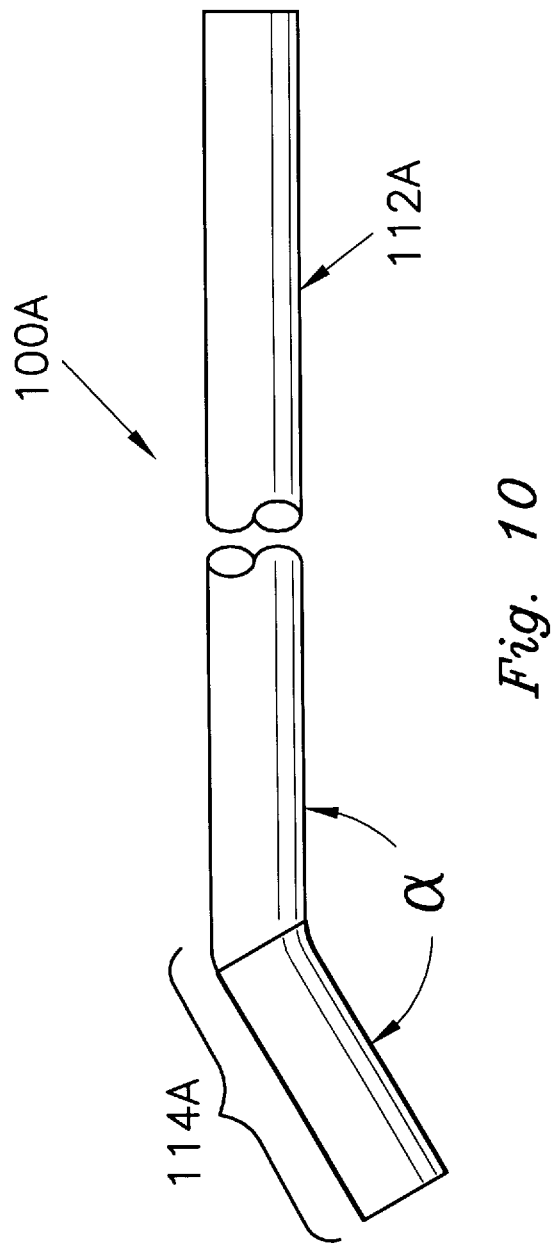

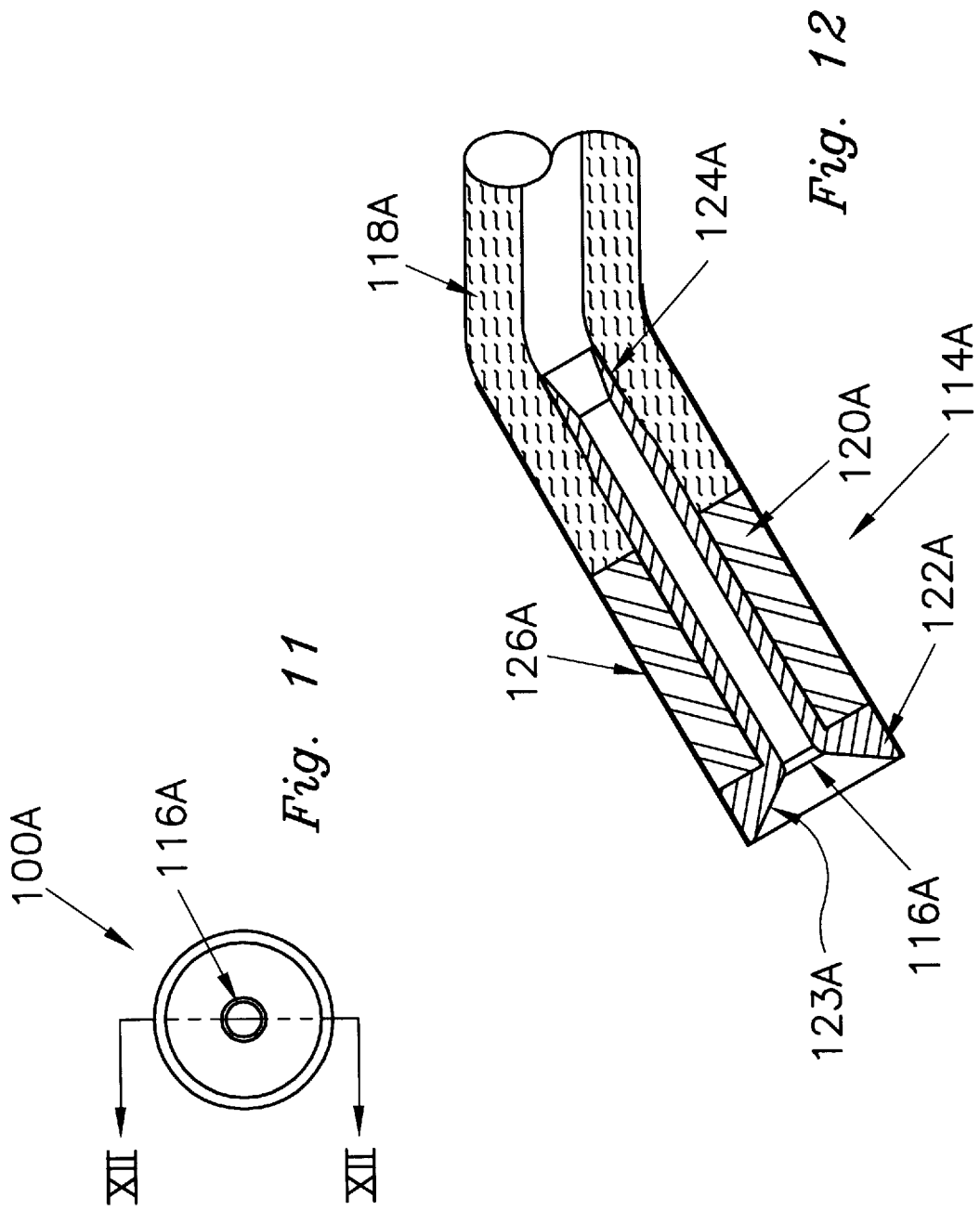

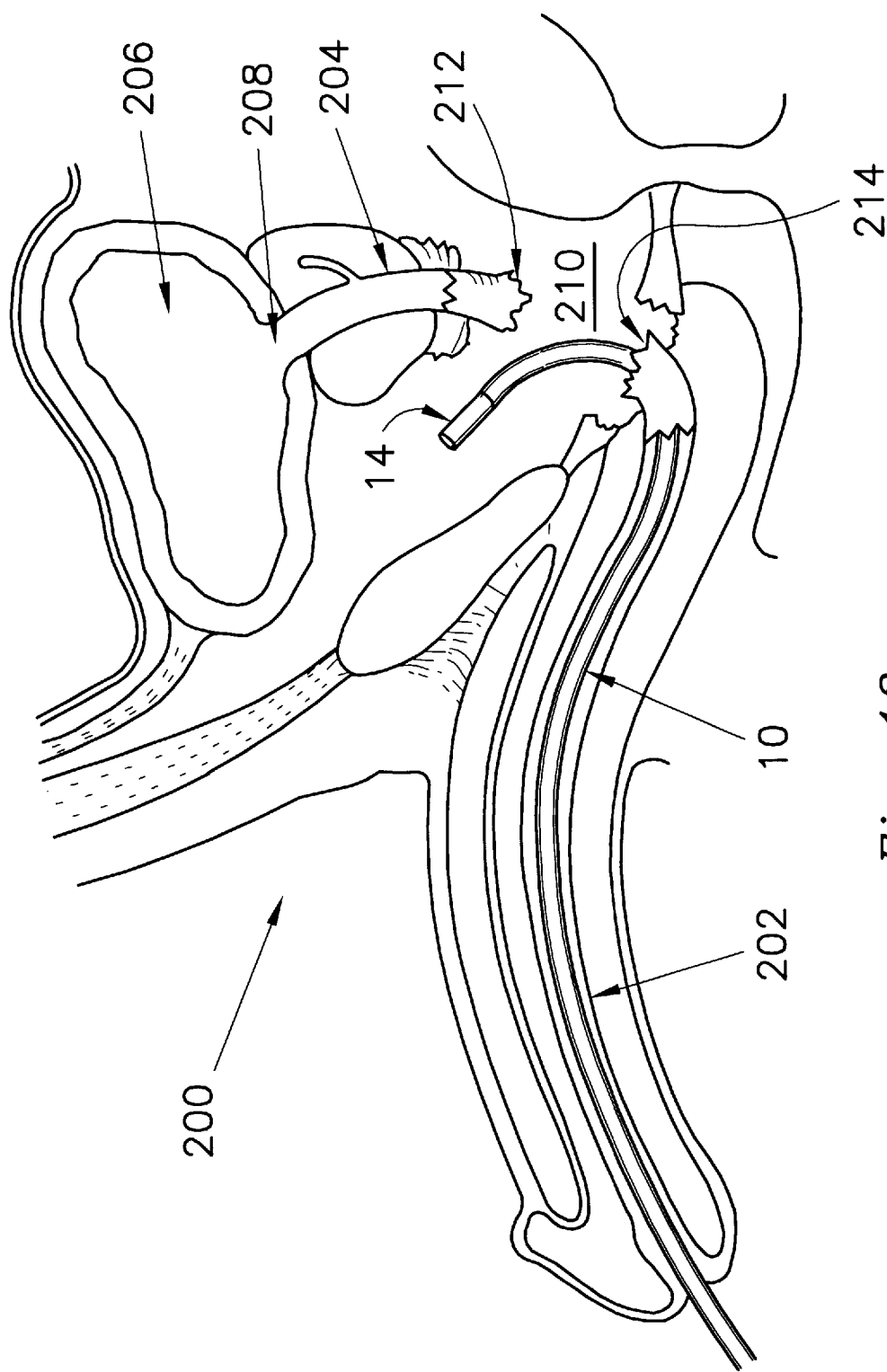

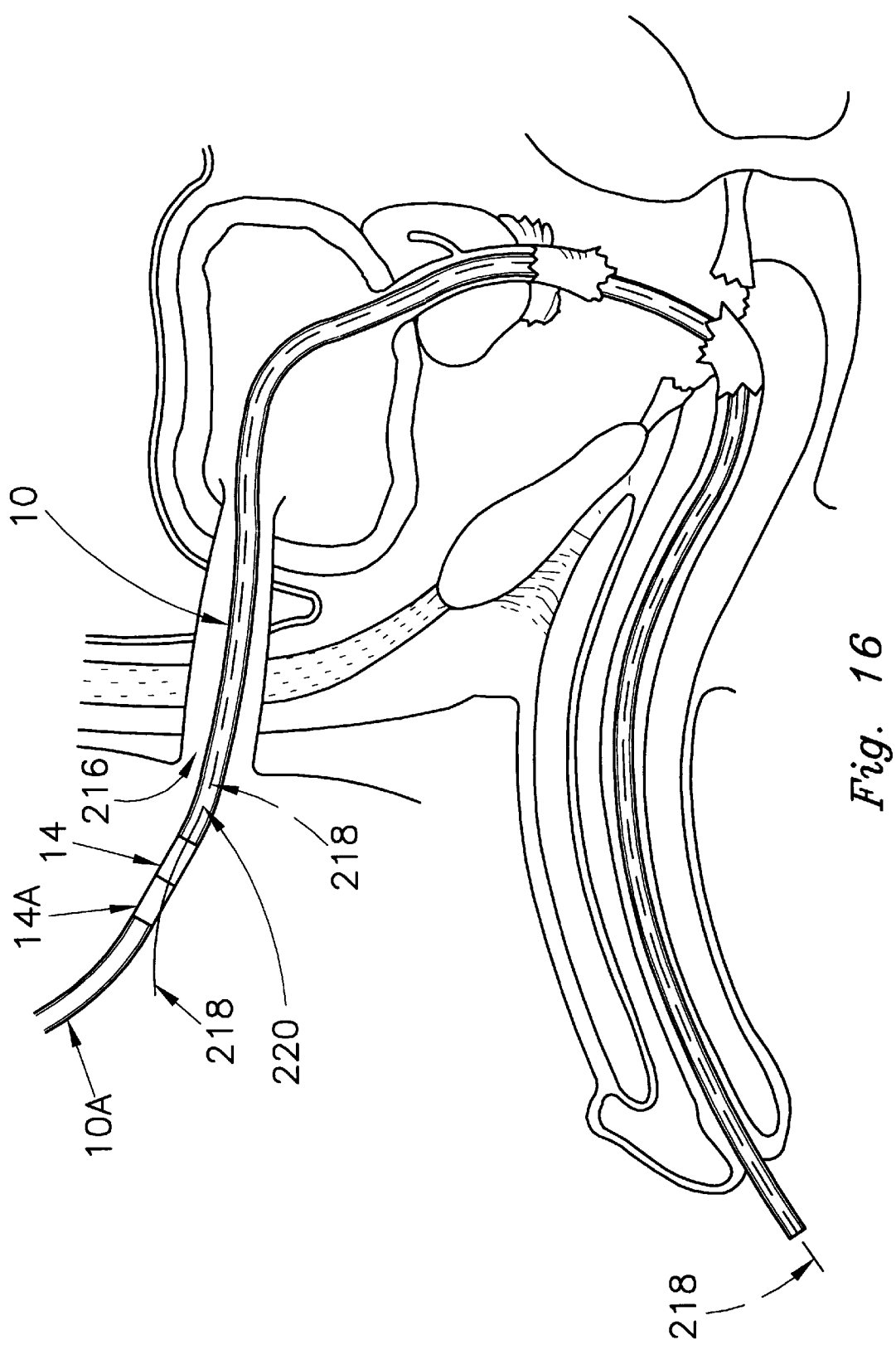

APPARATUS FOR ALIGNMENT OF TUBULAR ORGANS

BACKGROUND OF THE INVENTION

This invention relates to an apparatus for aligning a damaged tubular organ. In particular, it relates to a kit for tubular organ alignment for subsequent surgical repair.

FIELD OF THE INVENTION

The need often arises to repair completely or partially severed or otherwise damaged tubular organs (such as the urethra, veins, and ureters, for example). Such procedures require the surgeon to accurately locate the damaged ends of tubular organ segments and to bring the ends into alignment with one another. Such realignment can be challenging, especially in view of the tissue trauma and poor visibility often accompanying tubular organ injury.

For example, it is estimated that posterior urethral injury secondary to blunt trauma occurs in about 5–10% of men sustaining pelvic fractures. Such injuries can cause considerable morbidity including urinary incontinence, erectile dysfunction, and urethral stricture disease. Unfortunately, such complications can lead to chronic disability that may result in long term emotional and physical distress as well as significant financial loss.

Urethral disruption is often treated by a procedure known as open primary urethral alignment. However, open realignment procedures can be difficult due to extensive tissue trauma and the poor visibility often associated with pelvic bleeding. Also, the incidence of impotence and incontinence following open realignment procedures can be significant.

Another conventional procedure for correcting a urethral disruption has been suprapubic diversion with delayed urethroplasty. However, it has been discovered that suprapubic tube drainage before delayed urethroplasty can result in stricture formation in many cases. Also, it has been discovered that long term suprapubic tube drainage can sometimes lead to urinary tract infections, bladder calculi, tube leakage and dislodgement, and patient discomfort. Suprapubic tubes can also contaminate orthopedic hardware that may be used in early treatment of complex pelvic fractures.

More recently, the use of endoscopic and endourologic techniques soon after injury to repair urethral disruption have been explored. An example of such a procedure is described in *Urologic Surgery* (James F. Glenn, Editor, published by Harper & Row of Hagerstown, Md., 1975) at pages 688–696. Such techniques have been successful in that they eliminate the need for long term suprapubic tube drainage and can reapproximate the severed ends of a damaged urethra before significant malalignment can occur. Also, such techniques help to avoid the pelvic hematoma that can be caused by pelvic fractures, thereby decreasing the risk of further bleeding and possible infection. Additionally, endoscopic techniques can reduce the rate of post-injury impotence, incontinence, and stricture formation as compared to other procedures. Nevertheless, even with the use of improved endoscopic techniques it has been discovered that the insertion of guidewires with subsequent catheterization can become difficult when the tissue damage is extensive.

Fluoroscopy techniques have been used for guiding the placement of catheters and/or guidewires through the damaged portion of a urethra. Such a technique is described in "Early Fluoroscopic Realignment for Traumatic Urethral Injuries" (Thomas A. Londergan et al), published in Issue 49 (1997) of Urology at pages 101–103. Although early fluoroscopic realignment can be a safe and effective method for treating severe traumatic urethral injuries, the manipulation required by such techniques can be risky in some cases.

Accordingly, there remains a demand for a device adapted for realignment of a damaged tubular organ such as a wholly or partially severed urethra.

OBJECTS OF THE INVENTION

Accordingly, it is an object of the invention to provide an apparatus that can be used for the realignment of damaged tubular organs.

It is another object of the invention to provide an apparatus for realigning damaged tubular organs in a manner that overcomes the disadvantages associated with prior art techniques.

Other objects will be apparent in view of the following description of the invention, the Figures, and the appended Claims.

SUMMARY OF THE INVENTION

An apparatus is provided for realigning a damaged tubular organ for subsequent repair. The apparatus includes an elongated component that is adapted for insertion into a segment of the tubular organ and toward the damaged region of the tubular organ. The elongated component includes a body portion and a magnetically attractable element that is securely mounted adjacent to a distal end portion of the body. The apparatus also includes another elongated component that is also adapted for insertion, and which includes an elongated body and means for generating a magnetic field that is securely mounted adjacent to a distal end portion thereof. The means for generating a magnetic field should be sufficient to magnetically attract the magnetically attractable element of the other component.

The apparatus is adapted so that one of the components can be inserted into a segment of the damaged tubular organ toward the damaged region and the other component can be inserted into another segment of the tubular organ from the opposite side of the damaged region. As the components are guided toward the damaged region and toward one another, the means for generating a magnetic field in one of the components attracts the magnetically attractive element of the other component, and the components become connected along a substantially common axis in order to align the segments of the tubular organ along that axis.

The components are preferably tubular so that they define a passage through which a guidewire can be inserted. The magnetically attractable element can be formed from any material capable of being attracted by a magnet. Alternatively, it can itself provide a permanent source of a magnetic field. The means for generating the magnetic field can be a ferromagnetic material or an electromagnet, for example.

In use, the components are moved toward one another and are caused to engage one another along a substantially common axis under the influence of the magnetic field. Such engagement causes alignment of the segments of the tubular organ along the common axis. A procedure to repair the tubular organ can then be performed as damaged ends are maintained in axial alignment.

BRIEF DESCRIPTION OF THE DRAWINGS

FIGS. 1–6 illustrate an embodiment of an apparatus according to this invention: FIG. 1 is a side view of a component of the illustrated apparatus; FIG. 2 is an end view of the component shown in FIG. 1; FIG. 3 is a cross-sectional side view of a portion of the component shown in FIG. 1; FIG. 4 is a side view of another component of the illustrated apparatus; FIG. 5 is an end view of the component shown in FIG. 4; and FIG. 6 is a cross-sectional side view of a portion of the component shown in FIG. 4.

FIGS. 7–12 illustrate another embodiment of an apparatus according to this invention: FIG. 7 is a side view of a component of the illustrated apparatus; FIG. 8 is an end view of the component shown in FIG. 7; FIG. 9 is a cross-sectional side view of a portion of the component shown in FIG. 7; FIG. 10 is a side view of another component of the illustrated apparatus; FIG. 11 is an end view of the component shown in FIG. 10; and FIG. 12 is a cross-sectional side view of a portion of the component shown in FIG. 10.

FIGS. 13–16 illustrate a preferred use of an apparatus according to this invention.

DETAILED DESCRIPTION OF THE INVENTION

Figure 3:
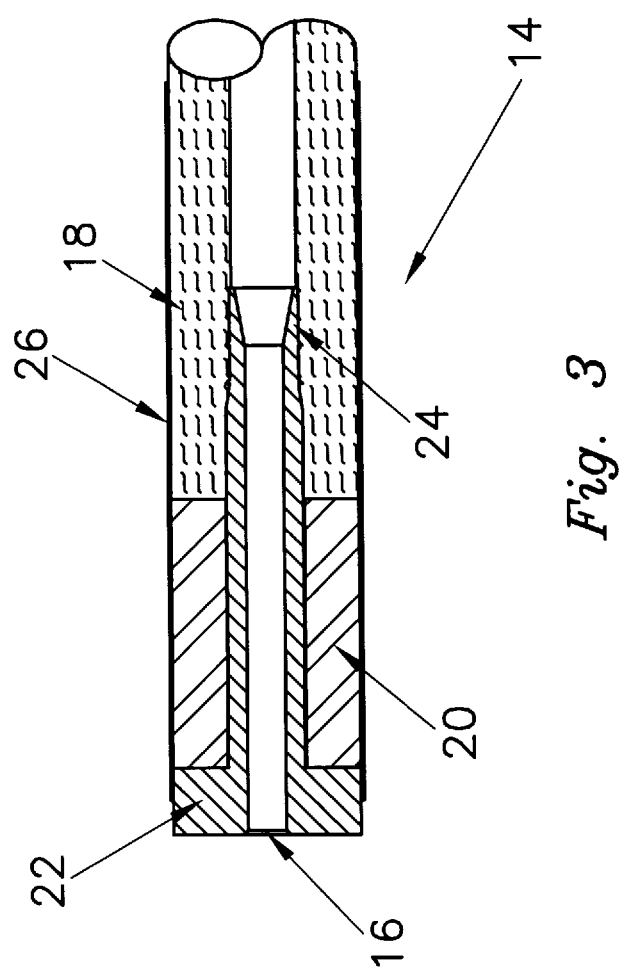

Preferred features of the invention will now be described with reference to several embodiments selected for illustration in the drawings. It will be appreciated that the invention is not limited to the embodiments selected for illustration, and that the drawings are not necessarily to scale. Also, although the invention is frequently described with reference to the repair of a wholly or partially severed urethra such as that caused by a traumatic pelvic injury, it will be appreciated that the invention also relates to the repair of other tubular organs (e.g., ureters, veins, and other substantially tubular or hollow organs) whenever alignment or realignment of such organs is desirable. Accordingly, the spirit and scope of this invention is not intended to be limited by the following description of preferred embodiments; instead, the invention is separately defined in the appended claims.

FIGS. 1–6 illustrate one embodiment of an apparatus according to this invention. The apparatus is preferably provided in the form of a kit that includes a first elongated component or catheter 10 (illustrated in FIGS. 1–3) and a second elongated component or catheter 10A (illustrated in FIGS. 4–6). Although catheters 10 and 10A are preferably separate components provided together in a kit, the catheters 10 and 10A can also be provided as single, continuous component with catheter 10 at one end and catheter 10A at the opposite end. For example, magnets or a magnet and a magnetically attractable material can be positioned at the opposite ends of a single elongated component with both ends being adapted for insertion into a surgical patient. In such a construction, the surgeon can be instructed to cut the elongated component into two separate lengths, each having a magnet or magnetically attractable material at one of its ends. Alternatively, a perforation can be provided along the continuous length so that the surgeon can easily separate it into two lengths. It is also contemplated that the apparatus can be provided and used in the form of a single elongated component wherein opposite ends are inserted and engaged to align a tubular organ, forming a continuous loop. If so, and if such an apparatus is adapted to accommodate the insertion of a separate component such as a guidewire, one or more holes can be provided along its length for the insertion and/or removal of the separate components. In any event, catheters 10 and 10A are each adapted for insertion into a surgical patient and into a tubular organ.

Referring specifically to FIGS. 1–3, catheter 10 includes an elongated body portion 12 having a distal end portion at 14. Although catheter 10 can be provided in any desired length, it should be sufficiently long for insertion into the surgical patient and into the tubular organ with at least a small portion of catheter 10 extending outwardly from the patient for manipulation by the surgeon. As shown in FIGS. 2 and 3, catheter 10 defines a longitudinal lumen or passage 16 that preferably extends throughout the entire length of catheter 10. Passage 16 is adapted in this embodiment for receiving a guide element such as a guidewire subsequent to insertion into the patient's tubular organ.

FIG. 3 illustrates details of a preferred construction for catheter 10, specifically at distal end portion 14. Catheter 10 includes a hollow component such as a tube 18 that extends along almost the entire length of catheter 10. Tube 18 is preferably flexible, but may be rigid if desired. Tube 18 may be formed from a thermoset material such as a silicone elastomer or may be formed from a thermoplastic elastomer such as the one sold under the trademark HYTREL ®, for example. Other materials, such as stainless steel, rigid thermoplastic, etc., may also be used so long as they are appropriate for surgical use, depending upon the specific surgical specialty or application for the device. The inner channel or lumen of the tubular member 18 (designated in FIGS. 2 and 3 as passage 16) may be centered or off-center when viewed from the end. Multiple lumens may be used as well. Although the surfaces of tube 18 are shown to be substantially smooth in the Figures, the inside or outside surfaces of the tube 18 may be grooved or contoured and the tube 18 may be formed into hooks, curls, tapers or any other shape dictated by a specific surgical application.

Catheter 10 also includes a cylindrical or ring-shaped or solid or otherwise configured magnet 20 that is most preferably positioned adjacent to the distal end of tube 18. As used herein, the term "magnet" is intended to encompass any component that is capable of generating a magnetic field or magnetic force. A magnet used in accordance with this invention may take a wide variety of forms although the magnetic field or force generated by the magnet should be sufficiently strong to attract a magnetically attractable material. The term "magnetically attractable material" is intended to encompass any metallic or polymeric material that is capable of attraction by a magnet whether or not it is itself a magnet capable of generating a permanent or temporary magnetic field. Most preferably, magnet 20 is formed from a permanently magnetic material such as neodymium or a neodymium alloy although any suitable or equivalent magnetic material can be substituted.

Alternatively, magnet 20 can be an electromagnet as opposed to a permanent magnet. In such an embodiment, an electromagnet can be placed in the tip portion of catheter 10 and any wires necessary for powering the electromagnet can be placed within tube 18 through additional channels or lumens incorporated for such use. An electric supply such as a transformer or batteries can then be connected to power the electromagnet.

A tip portion 22 is also provided at distal end portion 14 of catheter 10. Tip portion 22 includes a distal portion that extends to the distal end of catheter 10 as well as a portion of smaller diameter that extends through a passage in magnet 20 and into an interior passage of tube 18. Tip portion 22 is preferably engaged within tube 18, and a mechanical engagement between the tip and the tube is preferably provided. For example, a crimp ring or any other equivalent fastening means known in the art can be used to assist engagement. Also, tip portion 22 can be provided with one or more barbs on its shaft to prevent dislodgement. If a mechanical engagement is used, its form should match the materials and configurations of the tip and the adjacent structure. Accordingly, metal welds between metallic components can be used and plastic welds can be used to attach plastic components. Also, the engagement between the components should be adapted depending upon whether the elongated component (e.g., the "tube 18" in the illustrated embodiment) is hollow or solid, rigid or flexible, large or small, etc. Alternatively, an adhesive 24 such as an epoxy can be used to fixedly engage tip portion 22 to tube 18 to prevent separation.

Tip portion 22 captures magnet 20 so that it cannot move longitudinally or radially with respect to the end of tube 18. A through-hole in tip portion 22 cooperates to define a portion of passage 16, and a taper adjacent to the proximal end of the through-hole facilitates the insertion of a guide member such as a guidewire through tip portion 22 and outwardly through the distal end of catheter 10. Tip portion 22 is preferably formed from a metal that is suitable for contact with a surgical patient, although other materials can be substituted if desired.

Distal end portion 14 of catheter 10 also includes a cover 26 in order to seal the magnet 20 against contact with fluids and human tissues during a surgical procedure. Cover 26 also helps to securely affix the magnet to the catheter 10 so that it cannot be inadvertently dislodged during a surgical procedure. The material of cover 26 is preferably compatible with that of tube 18. Most preferably, cover 26 is formed from so-called "heat-shrink" tubing, the use of which is well known in the art. If cover 26 is formed from heat-shrink tubing, it is most preferably sized so that it shrinks into intimate engagement with the outer surfaces of tube 18, magnet 20 and tip portion 22 upon the application of adequate heat.

Figure 4:
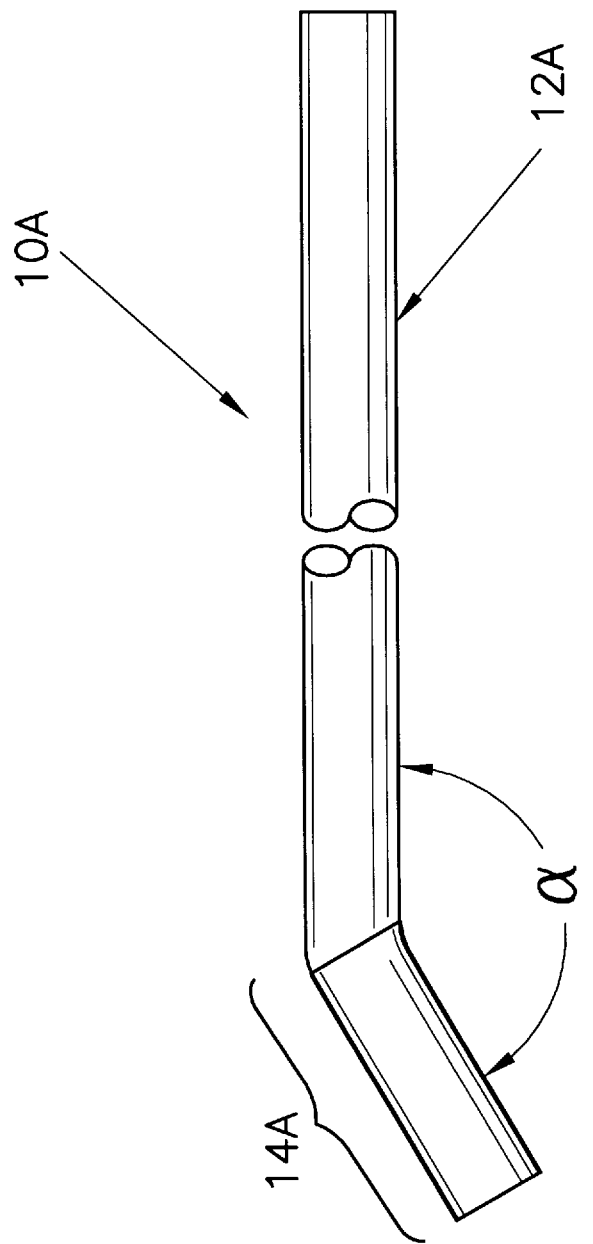

Referring now to FIGS. 4–6, catheter 10A is quite similar to catheter 10 in that it includes a body portion 12A, a distal end portion 14A, a passage 16A, a tube 18A, a magnet 20A, a tip portion 22A, an adhesive 24A and a cover 26A. Catheter 10A differs from catheter 10 in that distal end portion 14A includes a slight bend so that the axis of passage 16A is angled in distal end portion 14A relative to the axis in body portion 12A. The bend forms an angle designated "α" in FIG. 4, and angle α is preferably an obtuse angle between about 90° and 180°. The advantage of preferred angle α is to facilitate the surgeon's use of catheters 10 and 10A as will be described in further detail later. Otherwise, catheters 10 and 10A are substantially the same in structure and materials.

It is preferred for catheters 10 and 10A both to include magnets (items 20 and 20A, respectively) of substantially opposite poles so that they can attract one another in an end-to-end configuration during use, as will be described. Alternatively, one of the catheters 10 or 10A can have a magnetically attractable element that is not a magnet so long as the magnetic attraction between the magnet in the other catheter and the magnetically attractable element is sufficient to engage the catheters. In such an embodiment, magnet 20 or magnet 20A can be exchanged for a non-magnetic, magnetically attractable component.

FIGS. 7–12 illustrate another embodiment of an apparatus according to this invention. This apparatus embodiment preferably includes the combination of a catheter 100 and a catheter 100A in a kit. As with catheters 10 and 10A, these catheters are preferably separate components but may be formed at opposite ends of the same component, if desired. Other preferred characteristics and variations relating to the structure and materials of catheters 10 and 10A apply to catheters 100 and 100A as well, except for several exceptions to be explained.

Figure 8:
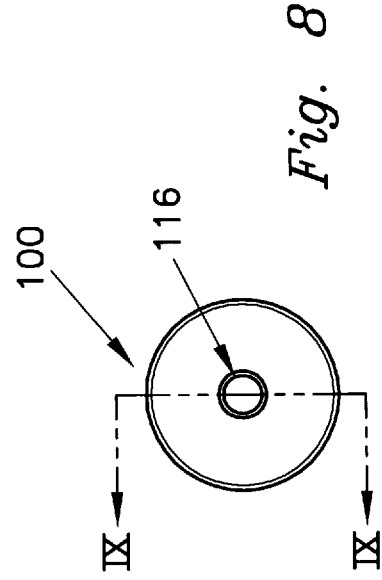
Figure 9:
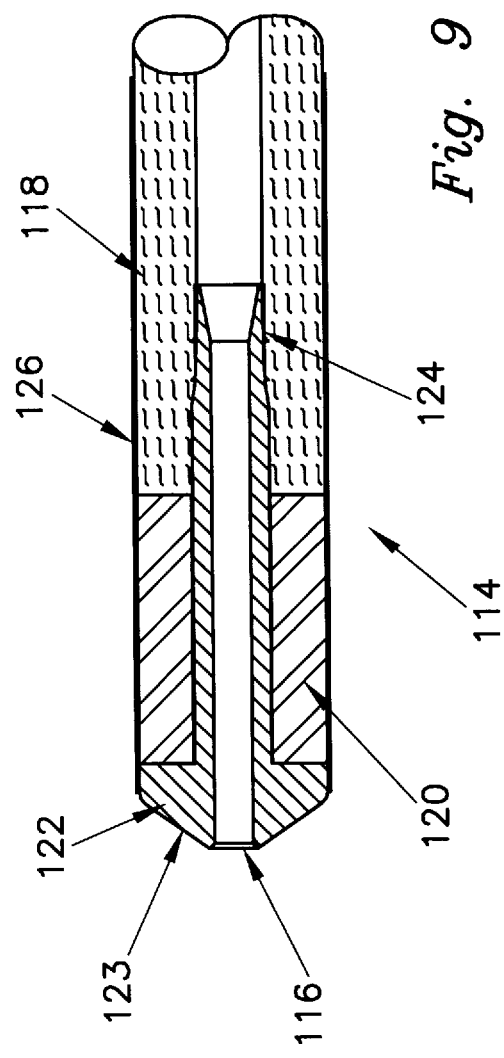

As shown in FIGS. 7–9, catheter 100 includes a body portion 112 that terminates at a distal end portion 114. FIGS. 8 and 9 illustrate a lumen or passage 116 that preferably extends throughout the length of catheter 100 to accommodate a guide member such as a guidewire. As shown in FIG. 9, distal end portion 114 of catheter 100 includes a tube 118, a magnet 120 and a tip portion 122 that is adhered to tube 118 with an adhesive 124 in order to capture and retain magnet 120. Distal tip portion 114 also includes a cover 126 to cover or encapsulate magnet 120. Tip portion 122 is similar to tip portion 22 except that it includes a tapered portion 123 in order to facilitate axial, end-to-end alignment of catheters 100 and 100A.

As shown in FIGS. 10–12, catheter 100A also includes a body portion 112A and a distal end portion 114A that, like distal end portion 14A, is oriented at an angle α with respect to body portion 112A. As shown in the cross-sectional illustration in FIG. 12, a passage 116A extends through catheter 100A. Also, distal end portion 114A of catheter 100A includes a tube 118A, a magnet 120A, a tip portion 122A, an adhesive 124A (or alternative mechanical engagement) and a cover 126A. Tip portion 122A includes a tapered recess 123A shaped to mate with tapered portion 123 of catheter 100. It will be appreciated that tapered portion 123 and tapered recess 123A facilitate the surgeon's alignment of catheters 100 and 100A so that the axis of passage 116 will be substantially continuous and unobstructed with respect to passage 116A. This of course can be highly desirable if a guidewire or other device is intended for insertion through the passageway so that it can extend through both catheters 100 and 100A without undue interference or restriction.

Although the apparatus of this invention has been described with reference to the specific embodiments illustrated in FIGS. 1–12, it will be appreciated that the device can take various forms and configurations without sacrificing the significant benefits of this invention. Together, catheters 10 and 10A form a catheter set for use during an alignment procedure. Catheters 100 and 100A likewise form a catheter set that is also adapted for use during an alignment procedure. In each catheter set, at least one catheter should have a magnet attached adjacent to its distal end portion. Accordingly, in each set one catheter can have a non-magnetic magnetically attractable element and the other catheter can have a magnet. The magnetically attractable element, if non-magnetic, can simply be a metal insert that is capable of magnetic attraction by the magnet in the other catheter. Alternatively, both catheters of a set can be provided with a magnet. For example, opposite-poled magnets would serve to strengthen the magnetic attraction between the tips.

The "male female" conical configuration of catheters 100 and 100A can be provided with various configurations in order to center or otherwise position one of the catheters with respect to the other along a substantially shared axis. Additional tip configurations such as "keyed" tips, angled tips and other mating shapes would also be appropriate. Similarly, the outer diameter of the tubular members used in catheters 10, 10A, 100 and 100A can be stepped or tapered or otherwise varied to allow the use of the device on tubular organs of various sizes or for passage of the catheters through strictures or other obstructions that may be encountered in a tubular organ. Also, it is contemplated that fixed or movable guidewires or stylets or obturators can be pre-placed in one or both of the catheters in order to prevent the ingress of tissue and/or body fluids into the catheter interior while they are being placed. They can also provide an indication of alignment between the catheters when extended into the end of the adjacent catheter. Such components should be removable if a guidewire or other component is intended for subsequent insertion.

Additional embodiments include the use of solid flexible or rigid rod-like members rather than tubular or hollow members for the catheter body portions. Any of the previously-described embodiments can be constructed using such solid members although such construction may preclude the use of a coaxial guidewire. Also, although one catheter of each of the catheter sets shown in the Figures is provided with a bend adjacent to or along the distal end portion, it is of course contemplated that both catheters of a set can be angled or substantially straight when relaxed. It is also contemplated that, although the ends preferably engage one another in an end-to-end configuration along the same axis, the ends can also be adapted to engage one another so that they are side-by-side or so that their respective lengths overlap with one another at their , distal end portions. In such a side-by-side configuration, the axes of the ends will be parallel at the end portions, but the components as a whole still share a substantially common axis.

A method of using the apparatus according to this invention will now be described with reference to FIGS. 13–16. In general, the apparatus is intended for use by surgeons in a wide variety of medical specialties to help approximate the damaged ends of tubular organs. The procedure described here for purposes of illustration relates to the alignment of a urethral disruption such as that caused by a severe traumatic pelvic injury. Essentially, the surgeon feeds the distal end of one of the catheters into the tubular organ through an incision or a natural opening. The distal end portion of the corresponding catheter is then fed into the disconnected section of the tubular organ, through a separate incision or natural opening. As the distal tips of the catheters are moved toward the damaged ends of the organ, they will exit the respective sections of the organ and "find" each other due to the magnetic attraction between their tips. When the organ ends are located and identified in this manner, they can be joined (using an anastomosis procedure, for example) and/or a stent or catheter may be placed to bridge the gap between the ends of the tubular organ and to hold them in substantial alignment while the tissue heals.

Referring to FIG. 13, a portion of a surgical patient is generally designated by the numeral "200". Due to a pelvic injury, the patient's urethra is severed into distinct and separated segments. Here, the numeral "202" represents an anterior or downstream segment of the patient's urethra and "204" represents a posterior or upstream segment of the urethra. The upstream segment 204 is connected to the patient's bladder 206 at a bladder neck 208. As shown, there is a complete urethral disruption 210 between a downstream end 212 of the upstream segment 204 and an upstream end 214 of the downstream segment 202.

Although a complete urethral disruption 210 is shown in FIG. 13, the disruption may be partial in that the segments 202 and 204 of the urethra may be at least partially connected in some way although otherwise damaged. Whether completely or only partially disrupted (or even completely connected), the urethra can be realigned using the apparatus according to this invention.

Figure 14:
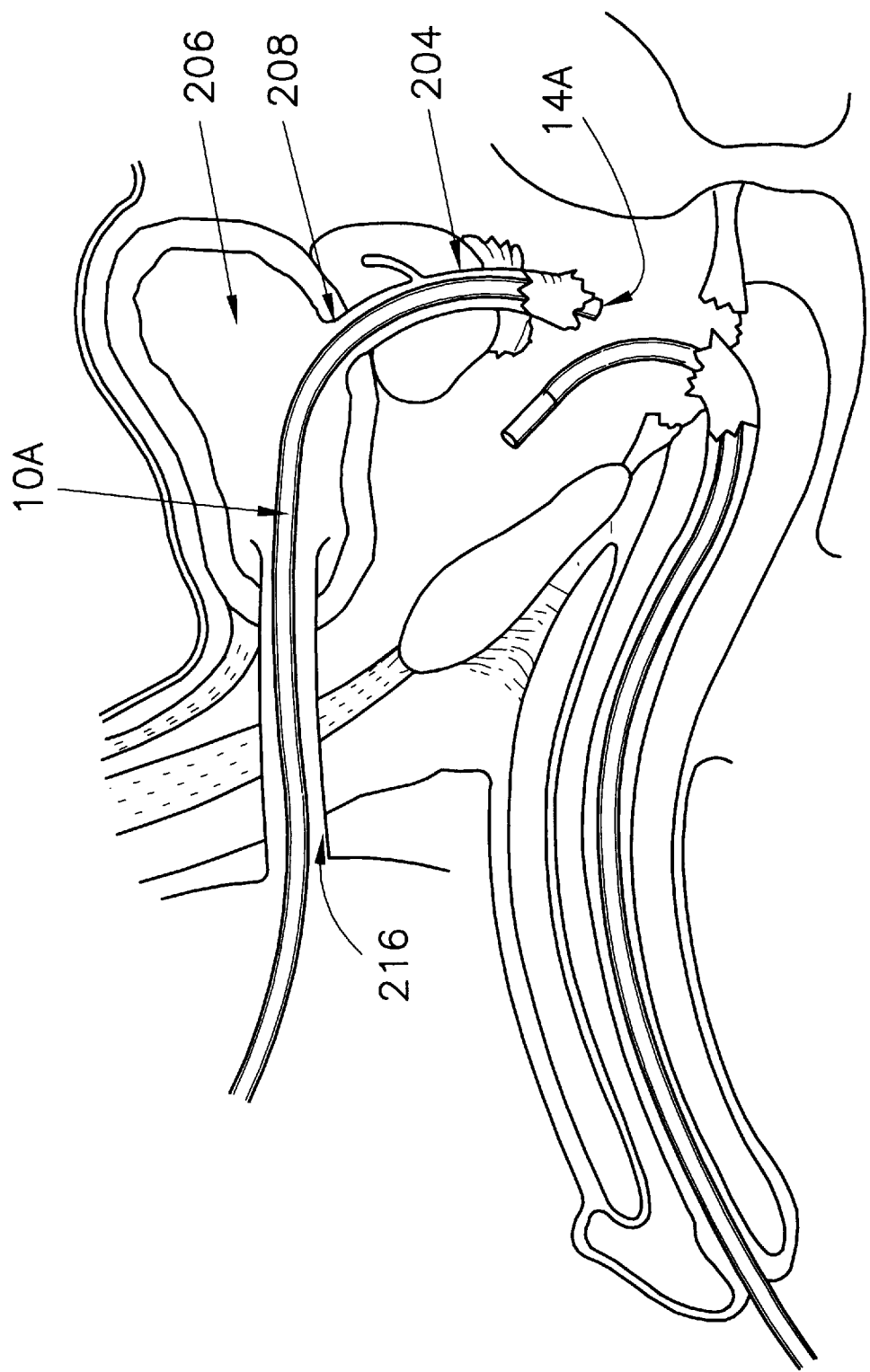

FIG. 13 also illustrates the positioning of a catheter such as catheter 10 through the downstream segment 202 of the patient's urethra, which is accomplished by inserting the distal end of catheter 10 upstream through the natural opening of the urethra until the distal tip portion 14 of catheter 10 extends into the region of the urethral disruption 210. As shown in FIG. 14, an incision 216 is formed in the pelvic region of the surgical patient for external access to bladder 206. Catheter 10A is then inserted, distal end portion first, through the incision 216, into the bladder 206, through bladder neck 208 and through upstream segment 204 of the patient's urethra until the distal end portion 14A of catheter 10A extends into the region of the urethral disruption 210.

Figure 15:
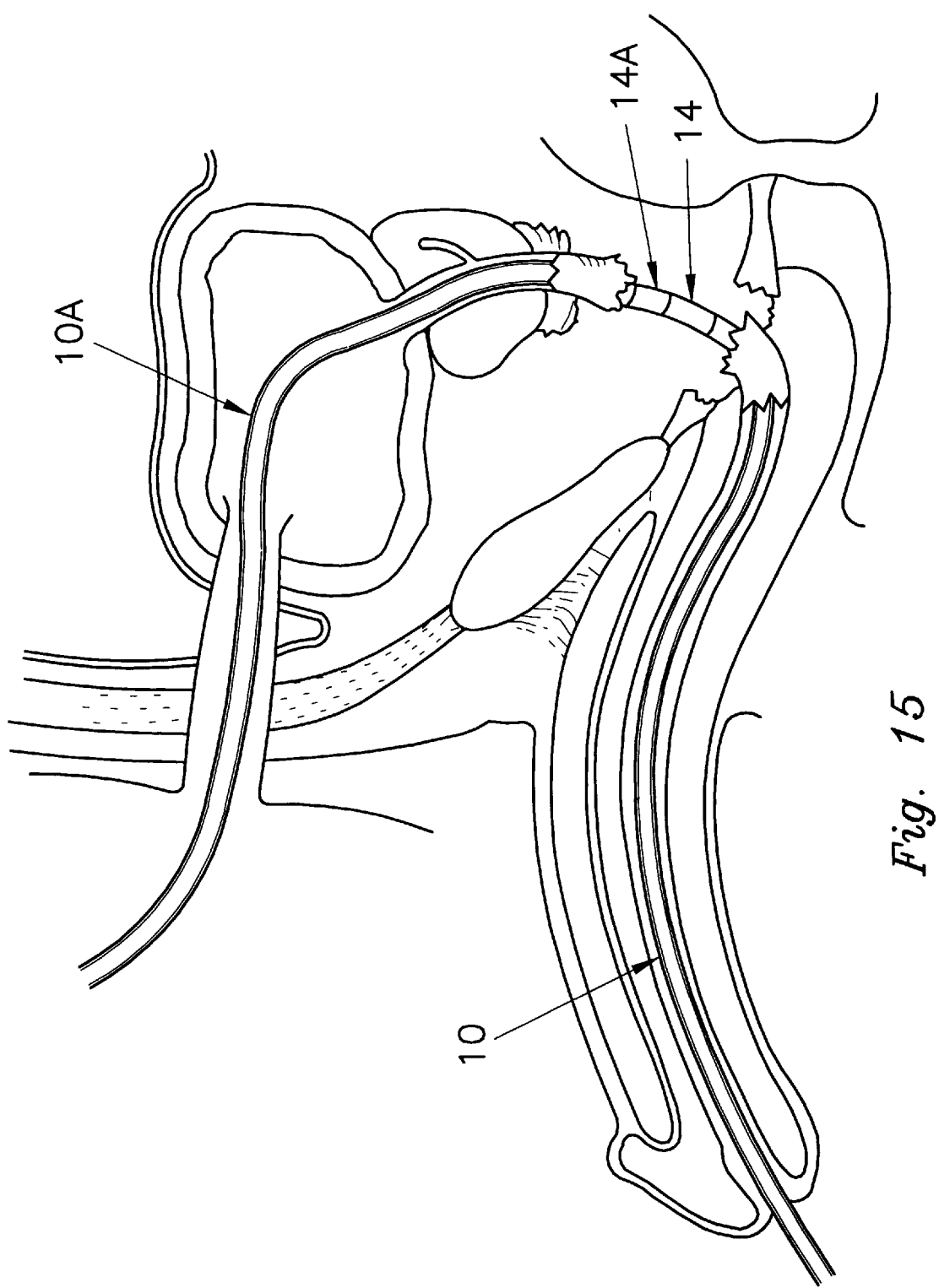

As shown in FIG. 15, the magnetic attraction between the distal end portions 14 and 14A of catheters 10 and 10A, respectively, causes the distal ends of catheters 10 and 10A to "find" one another in the region of the urethral disruption 210. It will be appreciated that the preferred bend in distal end portion 14A of catheter 10A (FIG. 4) assists the surgeon with the axial alignment of the catheters. Specifically, rotation of catheter 10A causes movement of its distal tip through a larger radial area because of the bend. Such rotation combined with longitudinal movement of catheter 10A with respect to the urethra permits the surgeon to cover a larger area so that the distal tips can more easily find one another for magnetic engagement.

Especially when preferred metal tips such as tips 22 and 22A are provided on catheters 10 and 10A, respectively, the surgeon will be able to detect a magnetic connection between the catheters as their ends "click" together. Preferably, such connection can be heard by the surgeon and felt by the surgeon so that he or she knows that the alignment has been accomplished.

Referring now to FIG. 16, catheters 10 and 10A are passed through the patient's urethra and outwardly from the patient through incision 216 until both of their distal end portions 14 and 14A are outside of the patient and accessible to the surgeon. A proximal end of catheter 10 preferably still remains outside of the natural opening of the patient's urethra for access and manipulation. It will be appreciated that end portions 14 and 14A can also be moved outwardly through the natural urethral opening as opposed to incision 216.

As illustrated partially in phantom in FIG. 16, a guidewire 218 is inserted through an opening 220 that is preferably provided adjacent to the distal end portion 14 of catheter 10 (or through a similar opening in catheter 10A). The guidewire 218 is advanced through catheter 10 until it extends outwardly from the proximal end of catheter 10 for access and manipulation by the surgeon. Although not shown, catheters 10 and 10A can then be removed, leaving the guidewire 218 in place within the patient, so that subsequent repair procedures can be conducted by the surgeon and so that additional instruments or catheters or other devices can be inserted through the aligned urethra over the guidewire.

In this manner, the ends 212 and 214 of the disrupted urethra are substantially aligned along an axis so that they can be joined using an anastomosis procedure or another appropriate procedure and/or so that a stent or catheter can be inserted to bridge the gap between the ends 212 and 214 in order to maintain the urethra in alignment while the tissue heals.

The catheter set 100, 100A illustrated in FIGS. 7–12 can also be used to perform the alignment procedure described with reference to FIGS. 13–16. It will be appreciated that the tapered portion 123 of catheter 100 and the tapered recess 123A of catheter 100A cooperate to promote axial alignment of the catheters with respect to one another. As the catheter tips magnetically attract one another, the "male" taper 123 tends to center catheter 100 with respect to the "female" recess 123A of catheter 100A, thereby aligning the axis of passage 116 with that of the distal axis of passage 116A.

It will be appreciated that the apparatus according to this invention, although described with reference to the alignment of a disrupted urethra for purposes of illustration, can easily be adapted for alignment of other tubular organs. For example, the apparatus can also be beneficially used during cardiovascular or related procedures to align a disrupted vein or artery. If so, the apparatus can be formed in part from a metallic (solid or hollow) elongated component (similar in structure to a guidewire, for example) with a magnet or magnetically attractable element at its tip. The apparatus can also be beneficially used during gastroenteroligic procedures such as bowel resection or realignment or feed tube installation. Also, it is contemplated that both catheters can be inserted through separate natural openings in a patient's body or that both catheters can be inserted through separate surgical incisions.

It has been discovered that alignment procedures utilizing an apparatus according to this invention confer significant advantages. For example, in the context of urethral realignment, early realignment using magnetic urethral catheters has greatly simplified an otherwise difficult and sometimes morbid procedure. The technique can be performed without prior training and can be completed in as little as about 20 to 30 minutes. Also, any strictures that may occur subsequent to the procedure are likely to be easily correctable and to recur infrequently. Continence is likely to be maintained without an increase in the incidence of impotence as compared to other techniques, and the need for prolonged suprapubic catheters is virtually eliminated. It will be appreciated that significant benefits can also be enjoyed by applying the apparatus of this invention to the manipulation of other tubular organs as well.

While the apparatus of this invention has been described with reference to various preferred embodiments and applications and with reference to various modifications thereof, additional embodiments and modifications can be made by exchanging the materials and structures of the apparatus for equivalent materials and structures without departing from the spirit or scope of this invention, which is described separately in the following claims.

What is Claimed is:

1. An apparatus for aligning a disrupted tubular organ, said apparatus comprising:
   an elongated member adapted for insertion into one body entrance, into said disrupted tubular organ, and toward a disrupted region of said disrupted tubular organ, said elongated member comprising an elongated body and a magnetically attractable element mounted adjacent to a distal end portion of said elongated body;
   a complementary elongated member adapted for insertion into a different body entrance, into said disrupted tubular organ and toward said disrupted region, said complementary elongated member comprising an elongated body and means for applying a magnetic field sufficient to magnetically attract said magnetically attractable element, said means being mounted adjacent to a distal end portion of said elongated body of said complementary elongated member;
   wherein at least one of said elongated bodies is comprised of a tubular portion defining a passage along an axis through which a guide element may be inserted; and
   wherein said magnetically attractable elements of said elongated members are guideable toward one another until they are magnetically attracted to each other and thereby attach to each other while disposed along a substantially common axis to align said tubular organ to an orientation substantially along said axis.

2. The apparatus defined in claim 1, wherein at least one of said elongated bodies comprises a solid portion.

3. The apparatus defined in claim 1, wherein at least one of said elongated bodies is formed from a metallic material.

4. The apparatus defined in claim 1, wherein at least one of said elongated bodies is formed from a polymeric material.

5. The apparatus defined in claim 1, wherein at least one of said elongated bodies is substantially rigid.

6. The apparatus defined in claim 1, wherein at least one of said elongated bodies is substantially flexible.

7. The apparatus defined in claim 1, wherein said elongated member and said complementary elongated member are separate components.

8. The apparatus defined in claim 1, wherein said means for applying said magnetic field comprises an electromagnet.

9. The apparatus defined in claim 8, further comprising a power supply connected to said electromagnet.

10. An apparatus for aligning a disrupted tubular organ, said apparatus comprising:
    an elongated member adapted for insertion into one body entrance into said disrupted tubular organ and toward a disrupted region of said disrupted tubular organ, said elongated member comprising an elongated body and a magnetically attractable element mounted adjacent to a distal end portion of said elongated body;
    a complementary elongated member adapted for insertion into a different body entrance, into said disrupted tubular organ and toward said disrupted region, said complementary elongated member comprising an elongated body and means for applying a magnetic field sufficient to magnetically attract said magnetically attractable element, said means being mounted adjacent to a distal end portion of said elongated body of said complementary elongated member;
    wherein said elongated bodies are connected to one another along a continuous length with said magnetically attractable element at one end of said continuous length and said means for applying a magnetic field at an opposite end of said continuous length;
    wherein at least one of said elongated bodies is comprised of a tubular portion defining a passage along said axis through which a guide element may be inserted; and
    wherein said magnetically attractable element of said elongated member and said means for applying a magnetic field of said complementary elongated member of said apparatus are guidable toward one another until they are magnetically attracted to each other and thereby attach to each other while disposed along a substantially common axis to align said tubular organ to an orientation substantially along said axis.

11. The apparatus defined in claim 10, wherein said continuous length member is separable prior to use, forming a separation between said elongated member and said complementary elongated member.

12. The apparatus defined in claim 1 or 10, further comprising means for preventing the ingress of solids or liquids into said tubular portion of said elongated body.

13. The apparatus defined in claim 1 or 10, wherein said magnetically attractable element and said means for applying a magnetic field are at least partially covered to prevent contact between said magnetically attractable element and said tubular organ and between said means and said tubular organ.

14. The apparatus defined in claim 1 or 10, wherein said magnetically attractable element comprises a metallic material.

15. The apparatus defined in claim 1 or 10, wherein said magnetically attractable element comprises a ferromagnetic material.

16. The apparatus defined in claim 1 or 10, wherein said means for applying said magnetic field comprises a ferromagnetic material.

17. The apparatus defined in claim 16, wherein said ferromagnetic material is selected from the group consisting of neodymium and a neodymium alloy.

18. The apparatus defined in claim 1 or 10, wherein said magnetically attractable element is substantially cylinder-shaped.

19. The apparatus defined in claim 1 or 10, further comprising a tip portion engaged to retain said magnetically attractable element with said means for applying a magnetic field.

20. A kit for aligning a disrupted tubular organ for subsequent repair, said kit comprising:

an elongated tubular member adapted for insertion into one body entrance into said disrupted tubular organ and toward a disrupted region of said disrupted tubular organ, said elongated member comprising an elongated body and a magnetically attractable element said magnetically attractable element being mounted adjacent to a distal end portion of an elongated member;

a complementary elongated tubular member adapted for insertion into a different body entrance, into said disrupted tubular organ, and toward said disrupted region, said complementary elongated member having a magnet, said magnet having a magnetic field sufficient to magnetically attract said magnetically attractable element, said magnet being mounted adjacent to a distal end portion of an elongated member;

wherein said elongated members are comprised of a tubular portion defining a passage along an axis through which a guide element may be inserted; and wherein said magnetically attractable element and said magnet are guideable toward one another until said magnet is magnetically attracted to said magnetically attractable element and joins said magnet and said magnetically attractable element along a substantially common axis to align said segments of said disrupted tubular organ in an orientation substantially along said axis.

21. A kit for aligning segments of a disrupted tubular body organ for subsequent surgical repair, wherein a gap is defined between portions of said segments, said kit comprising:

an elongated member adapted for insertion into one of said segments of said disrupted tubular organ and into said gap between said segments, said elongated member having a magnetically attractable element mounted adjacent to a distal end portion of said elongated member;

a complementary elongated magnetic member adapted for insertion into another segment of said disrupted tubular organ and into said gap between said segments, said complementary elongated member having means for applying a magnetic field sufficient to magnetically attract said magnetically attractable element, said magnetic means being mounted adjacent to a distal end portion of said complementary elongated member;

wherein at least one of said elongated members is comprised of a tubular portion defining a passage along an axis through which a guide element may be inserted; and wherein said magnetically attractable element and said magnetic means are guideable toward one another into said gap between said segments until said magnetic means magnetically attracts said magnetically attractable element and releasably engages said magnetically attractable element along a substantially common axis to align said segments of said disrupted tubular organ in an orientation substantially along said axis.

22. A kit for aligning segments of a disrupted tubular organ for subsequent repair, said kit comprising:

an elongated member having a proximal end and a distal end, said proximal end being adapted for insertion into one body entrance, into said disrupted tubular organ, and toward a disrupted region of said disrupted tubular organ, said distal end being adapted for insertion into another body entrance, into said disrupted tubular organ, and toward said disrupted region, said elongated member comprising an elongated body and a magnetically attractable element mounted adjacent to said proximal end of said elongated member, and means for applying a magnetic field sufficient to attract said magnetically attractable element mounted to said distal end of said elongated member;

wherein at least a portion of said elongated member is comprised of a tubular portion defining a passage along an axis; and wherein said magnetically attractable element of said elongated member and said means of said elongated member are guided toward one another until they are magnetically attracted to each other and thereby attach to each other while disposed along a substantially common axis to align said tubular organ to an orientation substantially along said axis.

\* \* \* \* \*